US011033707B2

(12) United States Patent
Andersson et al.

(10) Patent No.: US 11,033,707 B2
(45) Date of Patent: Jun. 15, 2021

(54) PORTABLE CONTROL DEVICE FOR REGULATING A CONTINOUS OXYGEN FLOW

(71) Applicant: LungFlex AB, Ljungby (SE)

(72) Inventors: Pär Andersson, Ljungby (SE); Kjell Henriksson, Bredaryd (SE); Bengt Hansson, Ljungby (SE)

(73) Assignee: LungFlex AB, Ljungby (SE)

( * ) Notice: Subject to any disclaimer, the term of this patent is extended or adjusted under 35 U.S.C. 154(b) by 450 days.

(21) Appl. No.: 15/764,608

(22) PCT Filed: Sep. 29, 2016

(86) PCT No.: PCT/EP2016/073179
§ 371 (c)(1),
(2) Date: Mar. 29, 2018

(87) PCT Pub. No.: WO2017/063891
PCT Pub. Date: Apr. 20, 2017

(65) Prior Publication Data
US 2018/0272100 A1    Sep. 27, 2018

(30) Foreign Application Priority Data
Oct. 12, 2015 (EP) ........................... 15189360

(51) Int. Cl.
*A61M 16/20* (2006.01)
*A61M 16/10* (2006.01)
(Continued)

(52) U.S. Cl.
CPC ...... *A61M 16/201* (2014.02); *A61M 16/0003* (2014.02); *A61M 16/0677* (2014.02);
(Continued)

(58) Field of Classification Search
CPC ...... F16K 31/52; F16K 31/54; F16K 31/5286; F16K 31/56; F16K 31/52408;
(Continued)

(56) References Cited

U.S. PATENT DOCUMENTS 3,332,439 A * 7/1967 Burke ................. A61M 39/283
137/556
3,949,966 A * 4/1976 Fabish .................. A61M 16/20
251/206
(Continued)

FOREIGN PATENT DOCUMENTS

| EP | 1090655 A1 | 4/2001 |
| EP | 2732841 A1 | 5/2014 |

(Continued)

OTHER PUBLICATIONS

International Search Report and Written Opinion for International Application No. PCT/EP2016/073179, dated Nov. 4, 2016 (4 pages).

*Primary Examiner* — Jan Christopher K Merene
*Assistant Examiner* — Cana A Gallegos
(74) *Attorney, Agent, or Firm* — Kagan Binder, PLLC

(57) ABSTRACT

A portable control device (10) for regulating a continuous oxygen flow to a user from an oxygen source, comprising: an inlet (11), to which the oxygen source may be fluidly connected; an outlet (12), to which a breathing device may be fluidly connected; a valve arrangement (20) fluidly connected to said inlet and to said outlet, said valve arrangement being adjustable between a maximum flow state corresponding to a maximum continuous flow of oxygen from the inlet to the outlet, and a minimum flow state corresponding to a minimum continuous flow of oxygen; and an actuator (13) movable between a maximum and a minimum position and being mechanically connected to the valve arrangement so that when said actuator is in the maximum position said valve arrangement is in the maximum flow state and when (Continued)

said actuator is in said minimum position said valve arrangement is in said minimum flow state.

15 Claims, 5 Drawing Sheets

(51) Int. Cl.
*A61M 16/06* (2006.01)
*F16K 31/528* (2006.01)
*F16K 3/02* (2006.01)
*A61M 16/00* (2006.01)

(52) U.S. Cl.
CPC .......... *A61M 16/101* (2014.02); *A61M 16/20* (2013.01); *F16K 3/0281* (2013.01); *F16K 31/5286* (2013.01); *A61M 2016/003* (2013.01); *A61M 2202/0208* (2013.01); *A61M 2205/3334* (2013.01); *A61M 2205/58* (2013.01); *A61M 2205/581* (2013.01); *A61M 2205/583* (2013.01); *A61M 2209/088* (2013.01)

(58) Field of Classification Search
CPC ...... F16K 31/524; F16K 7/061; A61M 16/20; A61M 16/201; A61M 39/22; A61M 39/28; A61M 39/283; A61M 16/0677; A61M 16/202; A61M 16/203; A61M 16/204; A61M 16/205; A61M 16/209; A61M 8/0816; A61M 8/0833; A61M 8/0875; G05D 7/00–0153

USPC .................................. 251/120, 123, 251–263
See application file for complete search history.

(56) References Cited

U.S. PATENT DOCUMENTS

| | | | |
|---|---|---|---|
| 4,139,017 A * | 2/1979 | Hamilton, Sr. ...... | A61M 39/283 137/343 |
| 4,241,896 A | 12/1980 | Clayton | |
| 4,366,947 A | 1/1983 | Clayton | |
| 4,645,175 A * | 2/1987 | Kamen ................. | A61M 39/28 251/9 |
| 4,787,406 A * | 11/1988 | Edwards .............. | A61M 39/283 137/1 |
| 6,189,531 B1 * | 2/2001 | Tatarek ................. | A61M 16/00 128/203.24 |
| 6,244,566 B1 * | 6/2001 | France ...................... | F16K 1/12 251/257 |
| 6,394,088 B1 | 5/2002 | Frye et al. | |
| 2010/0139656 A1 * | 6/2010 | Friberg ................. | A61M 16/20 128/204.21 |
| 2014/0182591 A1 | 7/2014 | Boone et al. | |
| 2016/0016018 A1 * | 1/2016 | Townsend .............. | F16L 37/02 128/201.23 |

FOREIGN PATENT DOCUMENTS

| | | | |
|---|---|---|---|
| WO | 9711734 A1 | 4/1997 | |
| WO | 9713185 A1 | 4/1997 | |

\* cited by examiner

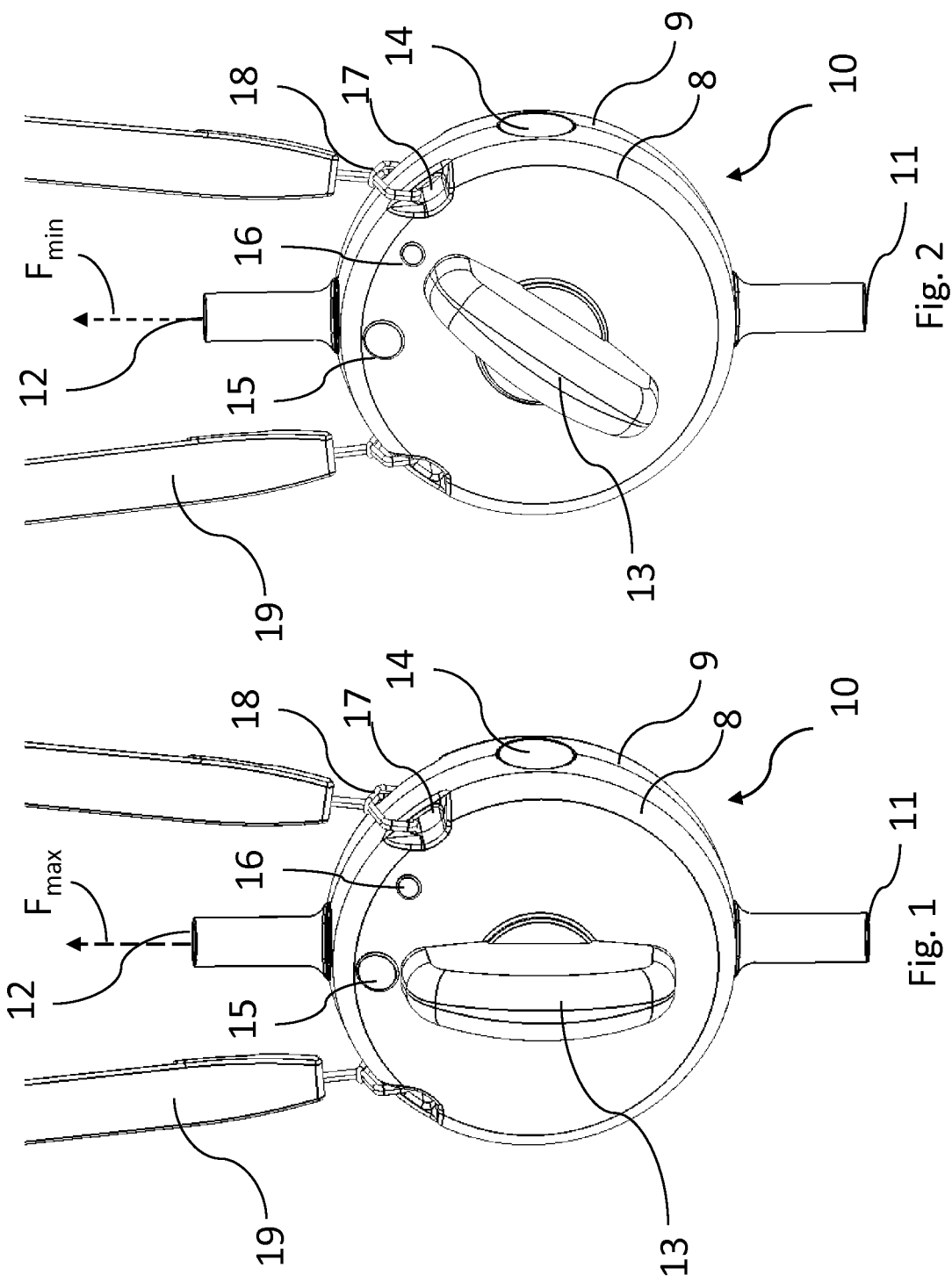

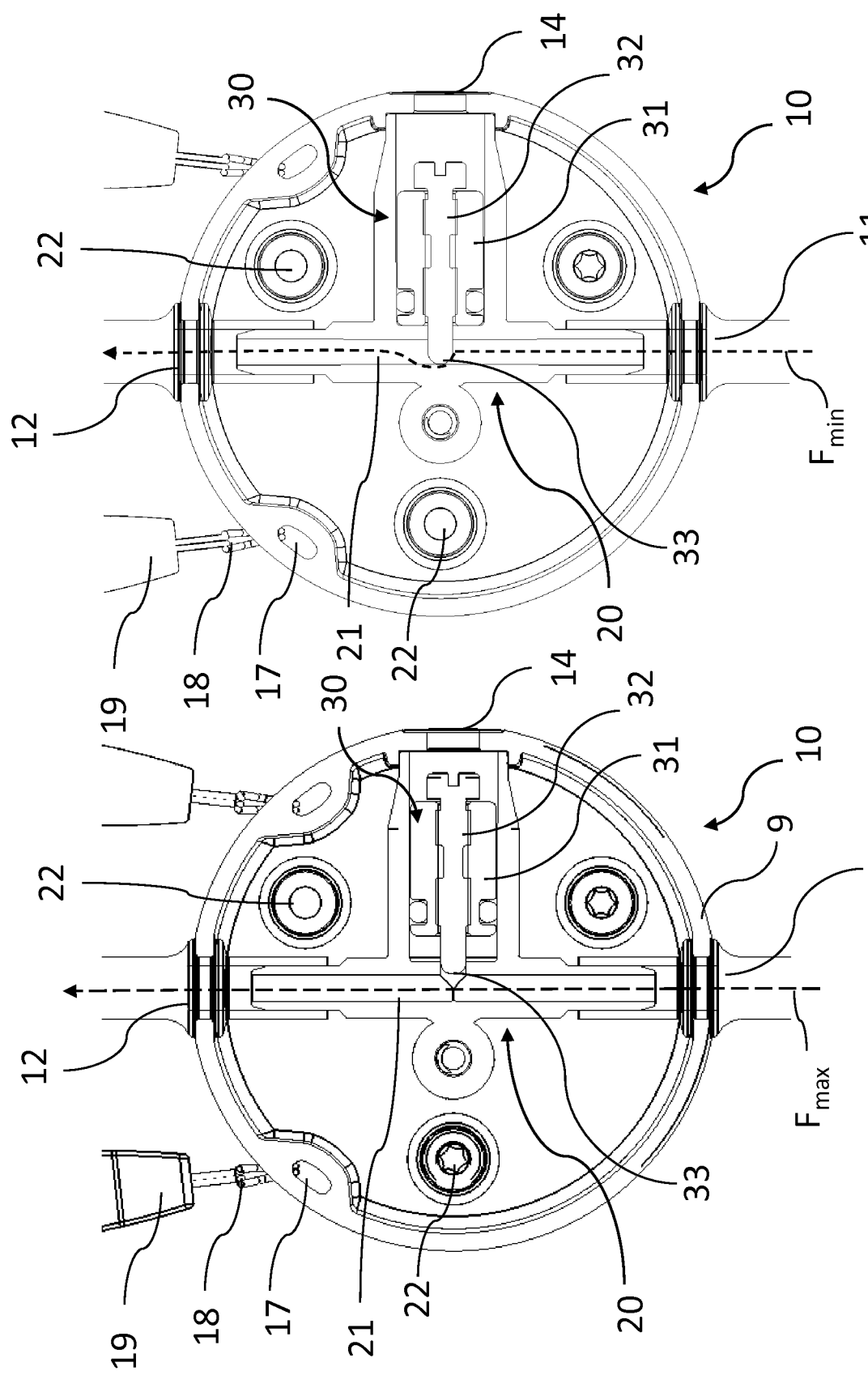

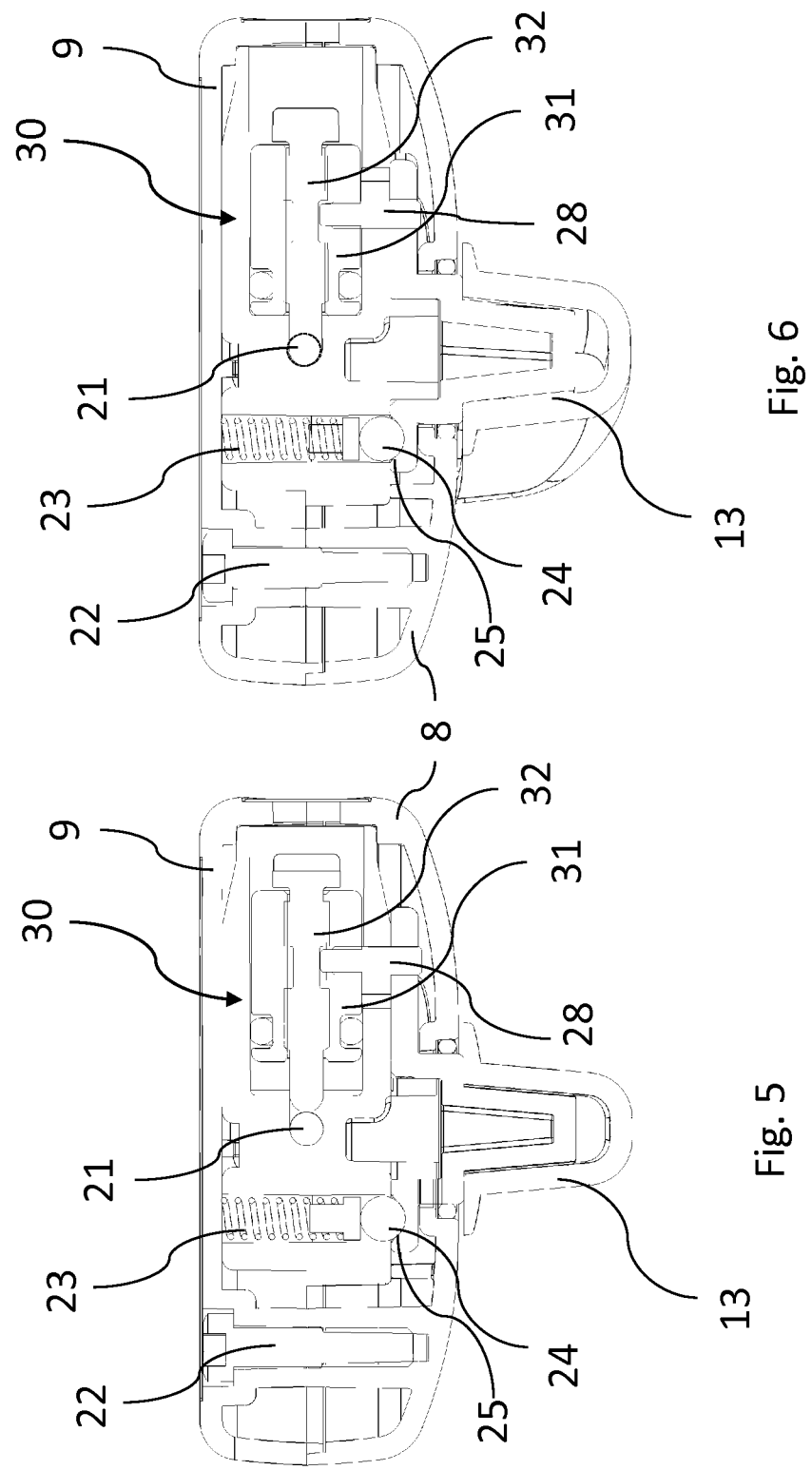

PORTABLE CONTROL DEVICE FOR REGULATING A CONTINOUS OXYGEN FLOW

CROSS-REFERENCE TO RELATED APPLICATIONS

This application claims priority to International Application No. PCT/EP2016/073179, filed Sep. 29, 2016, and titled "PORTABLE CONTROL DEVICE FOR REGULATING A CONTINUOUS OXYGEN FLOW", which in turn claims priority from European Application having Ser. No. 15/189, 360.9, filed on Oct. 12, 2015, both of which are incorporated herein by reference in their entireties.

TECHNICAL FIELD

The present invention relates to control devices for controlling the level of a continuous flow of oxygen from an oxygen source to a user. More specifically, the invention relates to portable control devices for above use that may be carried by the user during usage.

BACKGROUND OF THE INVENTION

Patients with respiratory diseases often need prescribed oxygen to keep the desired oxygen saturation level. If the level of oxygen saturation is too low, the patient's quality of life will be severely affected. The patient will experience discomfort, problems with sleep, social difficulties etc. At the same time, if the patient gets too much oxygen during a long period of time the patient's organs (such as the breathing organs mucous membrane) may be damaged and an increased risk for hypercapnia (abnormally elevated carbon dioxide levels in the blood which may be lethal) may occur. Therefore, medical personnel typically prescribe an amount (flow level) of oxygen to be used by the patient. The level is set so that an acceptable level of $PO_2$ (partial pressure of oxygen) and $CO_2$ in the blood is achieved at all times.

However, despite being an acceptable level, the patient will experience that the flow level of oxygen is satisfying for rest or some activities but not for other.

SUMMARY OF THE INVENTION

In view of the above-mentioned and other drawbacks of the prior art, the object of the present inventive concept is to provide a simple fail proof control device that provides an oxygen flow level which is right regardless of the activity of the patient.

The invention is based on the inventors' insight that keeping the desired $PO_2$, $CO_2$ level in the blood and/or measured $O_2$ by means of a $SPO_2$ meter for a user requires a control device that allows different flow of oxygen at different activity levels. However, with today's breathing systems, such as oxygen enrichers, would require a user, medical personal or kindred to adjust the level of oxygen flow on the (often distant) oxygen source, which involves a significant risk of that wrong amount of oxygen is supplied to the patient, which as explained above may be lethal. Further, for a patient to stand up, walk to the oxygen source and make such adjustment is a great effort for many patients and also involves risk of fainting and/or falling since moving lowers the oxygen level in the blood of the patient. Therefore, adjusting the oxygen in today's system is both dangerous, and requires 24/7 help for the user which is both expensive and limits the quality of life for the user.

The inventors' have further realized that the users of such a product typically will have a limited physique and fine motor ability, and therefore they have invented a portable control device for controlling the flow of oxygen which is simple for the user to handle and can be carried by the user at all times.

According to a first aspect of the invention there is provided a portable control device for regulating a continuous gas flow to a user from an oxygen source, said control device comprising: an inlet, to which the oxygen source may be fluidly connected, an outlet, to which a breathing device may be fluidly connected. Further the portable device comprise a valve arrangement fluidly connected to said inlet and to said outlet, said valve arrangement being adjustable between a maximum flow state corresponding to a maximum continuous flow of oxygen from the inlet to the outlet, and a minimum flow state corresponding to a minimum continuous flow of oxygen from the inlet to the outlet. Finally, the portable device comprises an actuator movable between a maximum and a minimum position and being mechanically connected to the valve arrangement so that when said actuator is in the maximum position said valve arrangement is in the maximum flow state and when said actuator is in said minimum position said valve arrangement is in said minimum flow state.

In the context of this application oxygen source should be understood as any type of device that can deliver oxygen in a higher concentration than the surrounding air, such as an oxygen concentrator, oxygen cylinder, liquid oxygen or the alike.

Moreover, breathing device should be understood as any type of device that can be used to breathe the oxygen, such as a nasal cannula or face mask or the alike.

Hereby, a control unit is provided which may easily be controlled with the actuator between the two different flows of oxygen is achieved. Further, the mechanical connection between the valve arrangement and actuator provides a fail-proof function which is not dependent on e.g. batteries or complicated by electrical buttons, thereby providing a simple handling for a user. Moreover, the portable device does not either include any electrical components that may fail and cause malfunction.

By providing the user with a portable control device that allows two different flows of oxygen, the user does not have to settle with one flow which is usually too high for rest and too low for performing an activity. Instead, the user may use the minimum oxygen flow during rest, so as to avoid the negative effects of breathing too much oxygen during long times. Further, the user may use the maximum oxygen flow during activity to avoid too low blood values (e.g. $PO_2$, $CO_2$, and/or $SPO_2$) when performing an activity, which would increase risk of accidents such as fainting/falling, experiencing discomfort etc. Thus, the portable control device increases the quality of life for the user.

Additionally, it also increases the quality of life of the relatives/care takers of the user, since the user may handle the device on his/her own and thereby will needs less help from others for performing simple tasks in the home. Moreover, since the portable control device will prevent users from falling or feeling discomfort in their homes, it is also probable to decrease the number of turn outs of emergency vehicles and personnel to the users, thus, saving money for the medical care system. Moreover, the patient will be able to perform tasks that would not be possible without different levels of oxygen flow for different tasks.

Moreover, one unexpected advantage of this system is that during the time the portable control unit is set to the minimum flow state, a pressure will build up between the valve arrangement and the oxygen source. When the actuator is subsequently turned to the maximum flow state a puff of oxygen is delivered to the user, since the built up pressure is released through the valve arrangement. This provides the user with a physical and audible confirmation that the maximum state is activated, and also provides the user with a bolus dose of oxygen, thereby making the portable control device even more efficient and safe.

Thus, a portable control unit according to above provides a fail-proof simple solution for a user to get the right amount of oxygen regardless of if user is at rest or is performing an activity.

In one embodiment, the maximum flow state of the valve arrangement is essentially an unrestricted flow from the inlet to the outlet, only limited by the dimensions of the breathing system.

In one embodiment the portable control unit is sized and adapted to be carried by a user. In yet one embodiment the portable device has a weight of less than 100 gram. In a preferred embodiment the portable device weight less than 80 gram. In another preferred embodiment the portable device weight less than 60 gram. Thereby, the user may carry the portable control device at all times without getting affected by its weight.

In one embodiment the minimum flow state of the valve arrangement allows an oxygen flow level that corresponds to a prescribed flow level for a patient when being at rest. Hereby, medical personnel may prescribe the right amount of oxygen flow specifically keeping an acceptable level of partial pressure of oxygen and/or $CO_2$ when the user is at rest.

In yet one embodiment the maximum flow state of the valve arrangement allows an oxygen flow level corresponding to a prescribed flow level for a patient performing an activity. Hereby, medical personnel may prescribe the right amount of oxygen flow specifically keeping an acceptable level of partial pressure of oxygen and/or $CO_{2\ Spo2}$ when the user is performing an activity.

In yet one embodiment the valve arrangement comprise a through hole fluidly connecting said inlet to said outlet, and said through hole having a substantially round cross-section when seen in a plane being perpendicular to the through hole's general extension.

In one embodiment the valve arrangement comprises a restricting means movable between a restricting position and an unrestricting position and wherein said restricting means restricts the oxygen flow from said inlet to said outlet when said valve arrangement is in the minimum flow state. Hereby, a mechanical restriction in the valve in the through hole may achieve the minimum oxygen flow, so as to provide a fail-proof mechanical restriction.

In yet one embodiment the restricting means is slidable between said restricting position and said unrestricting position. Thereby, the opening in the through hole for fitting the restricting means may be as small as possible, comparing with for example a pivoting movement of the restricting means.

In one embodiment the restricting means comprises tuning means for tuning the oxygen flow level through the valve arrangement in said minimum flow state. Hereby, medical personnel may measure the right amount of oxygen flow for the specific patient being at rest, and thereafter tune the minimum oxygen flow to correspond to that oxygen flow. Thereby, the user may be provided with the prescribed level by just turning the actuator to the minimum state.

In yet one embodiment the tuning means comprise a threaded sleeve and a tuning screw, wherein said tuning screw when screwed in a first rotational direction increases the possible oxygen flow level through the valve arrangement in said minimum flow state, and when screwed in a second rotational direction decreases the possible oxygen flow level through the valve arrangement in said minimum flow state. Thereby, medical personnel may easily tune the minimal flow by means of a tool, such as for example a screw driver or other suitable tool.

In one embodiment, the screw functions as the restricting element, restricting the oxygen flow in the through hole when the valve arrangement is in the minimum state.

In one embodiment, when in the valve arrangement is in the maximum state the screw is removed from the through hole and thus the tuning does affect the maximum flow.

In yet one embodiment the tuning screw is tightened to its inner end-position to achieve the lowest possible flow in the minimum flow state of said valve arrangement.

In yet one embodiment, the tuning screw and meshing threaded sleeve form a threaded fitting with thread friction. Hereby, the position of the tuning screw will not be affected by vibrations or other movements of the control device.

In one embodiment the tuning screw comprise a rounded screw tip having a radius corresponding to the through hole of said valve arrangement. Hereby, the rounded screw end may mesh with the through hole so as to seal the through hole from an oxygen flow.

In yet one embodiment the outer portion of said rounded screw tip is removed so as to always allow some flow of gas through the hole, even if the tuning screw is tightened all the way into the through hole. Hereby, the user will always have some flow of oxygen, even in the end position.

In one embodiment the actuator is restricted to two discrete possible positions, the first being the maximum position and the second being the minimum position. Hereby, the user can only maneuver the actuator into either the maximum position or the minimum position, thus increasing the safety further for the user.

In one embodiment, the actuator restriction is achieved by a spring loaded ball interacting with a groove having two seats and an intermediate ridge on said actuator. Hereby, if the actuator is brought into a position between the maximum position and minimum position the spring-loaded ball and interacting seat will force the actuator to either of the maximum or minimum position.

In one embodiment the actuator is movable in a rotating movement between the maximum position and the minimum position.

In yet one embodiment the actuator is movable in a slidable movement between the maximum position and the minimum position.

In one embodiment the portable control device comprise a safety seal so that the tuned minimum level may not be altered without breaking the safety seal. Hereby, the minimum level may not be altered after that the medical personnel has tuned the tuning screw to the prescribed flow level. This further increases the safety of the product and method.

According to another aspect of the invention there is provided an oxygen breathing system for providing a continuous oxygen flow to a user, comprising a portable control device according to any of the embodiments above, an oxygen source fluidly connected to the inlet of the portable control device via a tube, and a breathing device coupled to the outlet of the portable control device.

The advantages of the system as defined above are largely analogous to the advantages of the vehicle arrangement as described above. That is, it provides a fail-proof simple solution for a user to get the right amount of oxygen regardless of if user is at rest or is performing an activity.

According to another aspect of the invention there is provided a method for configuring a control device for regulating a continuous gas flow to a user from an oxygen source, wherein said method comprises the steps: determining a first desired oxygen flow to a user performing an activity, determining a second desired oxygen flow to a user resting. Further, providing a portable control device that, when in use, regulates a continuous gas flow to a user from an oxygen source, said control device having a valve arrangement adjustable between a maximal flow and a tunable minimal flow. Moreover, setting an oxygen flow level from the oxygen source so that it corresponds to the determined first desired oxygen flow, and tuning the minimum level of the control device so that it corresponds to the determined second desired oxygen flow. The advantages of the method as defined above are largely analogous to the advantages of the vehicle arrangement as described above. That is, it provides a fail-proof simple solution for a user to get the right amount of oxygen regardless of if user is at rest or is performing an activity. Moreover, by allowing medical personnel to measure and prescribe the maximum and minimum oxygen flow, the quality of life for the user will vastly increased when compared to having an average oxygen flow level prescribed regardless of level of activity.

In one embodiment, the oxygen breathing system is an oxygen enrichment system. Thereby, the system is optimized for people needing an increased concentration of oxygen to keep desired levels of $PO_2$, $CO_2$ in the blood and/or $SPO_2$ level.

Although the method includes a number of steps, these steps does not have to be conducted in any specific order. That is, although one step is described before the other one, it does not limit the invention to perform the step in said order. However, any step dependent on a previous step naturally needs to be conducted after any such step.

In one embodiment of the method, after tuning the minimum level of the control device, the device is safety sealed so that the tuned minimum level may not be altered without breaking the safety seal.

Hereby, the minimum level may not be altered after that the medical personnel has tuned it to the prescribed flow level. This further increases the safety of the product and method.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which:

FIG. 1 is a perspective view of a portable control device for regulating a continuous oxygen flow to a user wherein the actuator is in the maximum position, FIG. 2 is a perspective view of a portable control device for regulating a continuous oxygen flow to a user wherein the actuator is in the minimum position, FIG. 3 is a cross-sectional front view of a portable control device for regulating a continuous oxygen flow to a user wherein the valve arrangement is in a maximum flow state, FIG. 4 is a cross-sectional front view of a portable control device for regulating a continuous oxygen flow to a user wherein the valve arrangement is in the minimum flow state, FIG. 5 is a cross-sectional top view of a portable control device for regulating a continuous oxygen flow to a user wherein the valve arrangement is in a maximum flow state, FIG. 6 is a cross-sectional top view of a portable control device for regulating a continuous oxygen flow to a user wherein the valve arrangement is in the minimum flow state.

DETAILED DESCRIPTION

Figure 8:
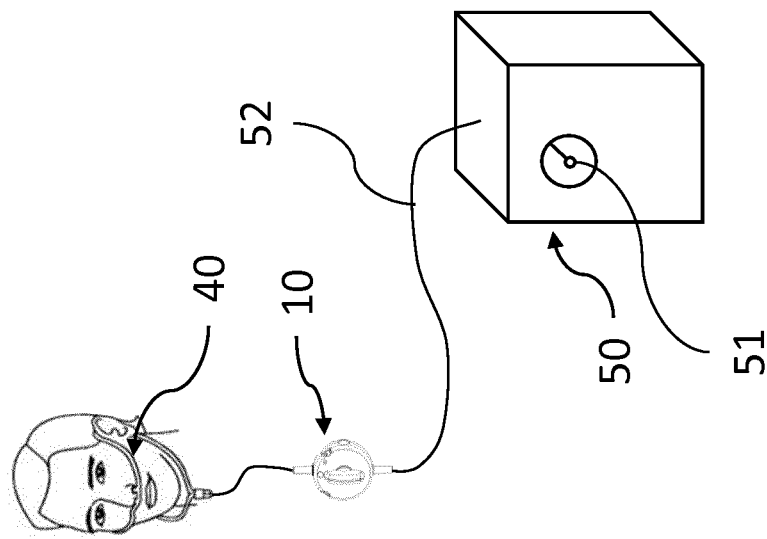
FIG. 8 is a schematic sketch of an oxygen breathing system.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

In the following, the portable control device is described to work together with an oxygen concentrator. However, any type of oxygen source that can deliver oxygen in a higher concentration than the surrounding air may be used, such as an oxygen concentrator or liquid oxygen or the alike.

Further, in the following, the face of the portable control device 10 comprising the actuator 13 is called the "front", and the opposite site the "back". Moreover, the side towards the outlet 12 is called the "top" and the side towards the inlet 11 is named the "bottom". Thus, a top view is seen from the side where the outlet 12 is places. These names should not be construed as limited to the inventive scope.

FIG. 1 and FIG. 2 are perspective views of the portable control device 10 for regulating a continuous oxygen flow to a user. In FIG. 1 the actuator 13 is in the maximum position. In FIG. 2 the actuator 13 is in the minimum position. The maximum position is indicated by a first indicator 15 and the minimum position is indicated by a second, smaller, indicator 16. The actuator is a rotational actuator. In the maximum position the actuator aligned in a top-bottom direction. In the minimum position the actuator 13 forms an angle (other than zero) relative the top-bottom direction. This is also indicated that the air passage is not aligned, thus restricted, when the actuator is in the minimum flow position.

In the illustrated embodiments, the portable control device 10 comprises a housing front portion 8 and a housing back portion 9. Further, the portable control device 10 comprises an inlet 11 placed on the bottom of the portable control device 10, for allowing oxygen to enter the control device 10 from the oxygen source 50 (FIG. 8). Further, the portable control device 10 comprises an outlet 12 placed on the top of the portable control device 10, for allowing oxygen to exit the control device 10 to the breathing device 40 (FIG. 8). Moreover, the portable control device 10 comprises a safety seal 14, for sealing the hole through which the minimum flow state may be tuned. Moreover, the portable control device 10 comprises an aperture 17 for connecting a holding device 19 via a wire loop 18. In the figures the holding device 19 is a strip so that the user may hang the device around his/her neck. Also, other carrying devices may be possible such at belt carriers, arm cases or other. Further, in FIG. 1 a maximum flow ($F_{max}$) is illustrated through the inlet 11 and out of the outlet 12. Similarly, in FIG. 2 a minimum flow ($F_{min}$) is illustrated through the inlet 11 and out of the outlet 12.

FIGS. 3 and 4 are cross-sectional front views of the portable control device 10. The cross-section in FIGS. 3 and 4 unveils the valve arrangement 20 which is in a maximum flow state in FIG. 3 and in the minimum flow state in FIG. 4. The valve arrangement comprise a through hole 21 fluidly connecting the inlet 11 to the outlet 12. Moreover, the valve arrangement 20 comprises restricting means 30 sized and adapted to allow a maximum oxygen flow $F_{max}$ when the valve arrangement is in the maximum flow state, se FIG. 3, and allow a minimum oxygen flow $F_{min}$ when the valve arrangement is in the minimum flow state, see FIG. 4.

Moreover, the restricting means 30 in the illustrated example is slidably moveable. However, in other embodiments, it may instead be pivotably moveable with the same function. Further, the restricting means 30 comprise a tuning means. The tuning means in the illustrated embodiments is a threaded sleeve 31 and a tuning screw 32. The threaded sleeve 31 is slidably arranged in the valve arrangement 20. Moreover, the tuning screw 32 may be accessed by means of a screw driver through a hole in the portable control device 10, over which hole the security seal 14 is places after tuning the tuning screw 32. The screw may have a standard screw head. However, it is also possible that the screw has a specialized screw head so that tuning can only be carried out with the right type of screw driver. Moreover, the tuning screw 32 has a rounded screw end 33. The screw end 33 has a radius corresponding to the inner radius of the through hole 21. Thereby, if the screw end 33 is brought against the inner wall of the through hole, the passage in the through hole is blocked by the tuning screws en portion. Moreover, in the illustrated example, the rounded screw end 33 has an outer portion which is removed (as shown in the flow line of minimum oxygen flow $F_{min}$ as it passes screw end 33) so as to always allow some flow of gas through the through hole 21, even if the tuning screw is tightened all the way against the inner wall of the through hole 21. In the illustrated embodiments, the portable control device 10 comprises a housing front portion 8 and a housing back portion 9. Moreover, the cross-sectional view in FIGS. 3 and 4 shows the sleeves and mounting screws 22 which holds the housing front portion 8 and a housing back portion 9 together.

FIGS. 5 and 6 are cross-sectional top views of the portable control device 10. The cross-section in FIGS. 5 and 6 also unveils the valve arrangement 20 which is in a maximum flow state in FIG. 5 and in the minimum flow state in FIG. 6. Other than illustrating the portable control device 10 including the restricting means 30, tuning screw 32 and sleeve 31 from a top-view, FIGS. 5 and 5 also unveils the mechanical construction restricting the actuator 13 to two discrete possible positions, the first being the maximum position and the second being the minimum position. This may be achieved in different ways, but in the illustrated embodiments the actuator 13 position restriction is achieved by a spring 23 and a ball 24 held in the valve arrangement 20. Said ball 24 is spring-loaded with the spring 23 so as to interact with a groove 25 in on a portion of the actuator, wherein the groove has two seats and an intermediate ridge. Thereby, if the actuator is only partly turned towards the other position, it will either be forced back to its original position or forced forward to the next position, depending on if the actuator has been turned passed the ridge or not.

Moreover, restriction means may be used to restrict the movement of the actuator so that it may not be moved past the two discrete positions. The restriction means may be the ends of the groove 27. The restriction means may also be a part of the housing front 8 and/or back 9 portions, such as in connection with the screw 22 holes in the housing.

Figure 7:
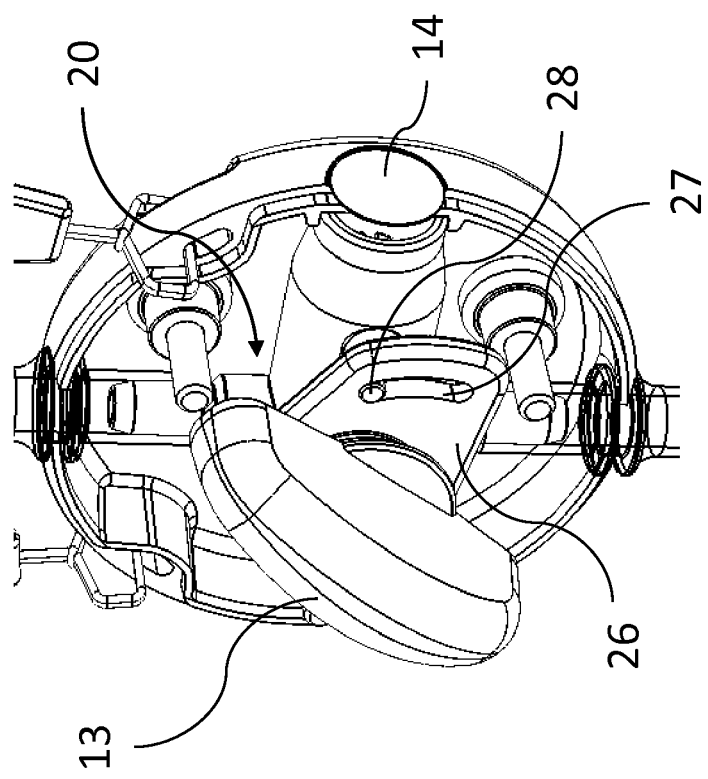
FIG. 7 is a cross-sectional front view showing the details of the mechanical connection between the actuator and the valve arrangement.

Moreover, FIG. 5, FIG. 6 and FIG. 7 illustrate the details of the mechanical connection between the actuator 13 and the valve arrangement 20. More specifically, a pin 28 is coupled in a first end portion with the restricting means 30, e.g. the threaded sleeve 31 and/or the tuning screw 32. Further, in the other end portion of the pin 28, the pin 28 meshes with a groove 27 of a base plate 26 of the actuator 13. The base plate 26 rotates together with the actuator 13 and the groove 27 is formed so as to slide the restricting means 30 into the through hole when from the maximum position to the minimum position.

Further, the pin 28 and the restricting means 30 may be glued together so as to always move together without any freedom to play. Moreover, the actuator 13 and the base plate 26 may be glued together so as to always move together without any freedom to play.

Further, FIG. 8 is a schematic sketch of an oxygen breathing system comprising a portable control device 10 as described above, an oxygen source 50 fluidly connected to the inlet 11 of the portable control device 10 via a tube 52, and a breathing device 40 coupled to the outlet 12 of the portable control device 10.

Figure 9:
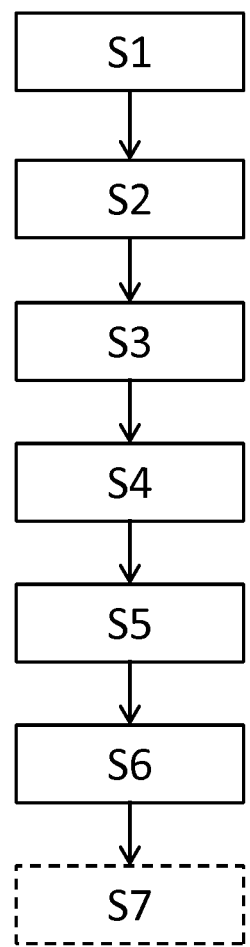
FIG. 9 is schematic overview of the method for configuring a control device (10) for regulating a continuous oxygen flow.

Finally, FIG. 9 is a schematic overview of the method for configuring a control device 10. The method includes a number of steps, which does not have to be conducted in any specific internal order. The method comprises the steps of determining S1 a first desired oxygen flow $F_{max}$ to a user performing an activity. This may be done by medical personnel, e.g. by measuring the $PO_2$ (partial pressure of oxygen), $O_2$ saturation or $CO_2$ in the blood during a certain activity. It is possible to measure blood gas through e.g. arterial blood gas or $O_2$ saturation with a pulse oximetry. Typically, this would be measured while walking or standing. However, if the patient is not able to walk it may be measured during rest. Throughout such a measuring the level of oxygen flow to the user may be varied and the $PO_2$ and/or $CO_2$ levels measures during the variation so as to find a flow that corresponds to a desired value. Also, the patients experienced comfort/discomfort may be used to determine a desired first oxygen flow. Moreover, the step of determining (S2) a second desired oxygen flow $F_{min}$ to a user resting should be performed. This may be conducted before or after the step of determining S1 the first desired flow. Moreover, this step may be conducted in an analogous way as described for the first step S1 above. Further, the method includes providing (S3) a portable control device 10 that, when in use, regulates a continuous gas flow to a user from an oxygen source, and wherein the control device has a valve arrangement that is adjustable between a maximal flow and a tunable minimal flow. Thereafter, the step of setting S5 an oxygen flow level from the oxygen source so that it corresponds to the determined first desired oxygen flow $F_{max}$, may be carried out. The final step is tuning S6 the minimum level of the portable control device 10 so that it corresponds to the determined second desired oxygen flow $F_{min}$. Again, to clarify, this step may be performed before setting S5 an oxygen flow level from the oxygen source.

Moreover, a optional step may be carried out, namely to, after tuning the minimum level of the portable control device 10, safety sealing S7 the portable control device 10 so that the tuned minimum level may not be altered without breaking the safety seal 14.

When using the portable control device, it is of course also needed to fluidly connecting the control device to the oxygen source and to a breathing device, so that it may be used.

The invention claimed is:

1. A portable control device (10) for regulating a continuous oxygen flow to a patient from an oxygen source, said control device comprising;
    an inlet (11), to which the oxygen source may be fluidly connected;
    an outlet (12), to which a breathing device may be fluidly connected;
    a valve arrangement (20) fluidly connected to said inlet (11) and to said outlet (12), said valve arrangement (20) being adjustable between a maximum flow state corresponding to a maximum continuous flow of oxygen (Fmax) from the inlet (11) to the outlet (12), and a minimum flow state corresponding to a minimum continuous flow of oxygen (Fmin) from the inlet (11) to the outlet, and
    an actuator (13) movable by a patient between a maximum and a minimum position and being mechanically connected to the valve arrangement (20) so that when said actuator (13) is in the maximum position said valve arrangement (20) is in the maximum flow state and when said actuator (13) is in said minimum position said valve arrangement (20) is in said minimum flow state;
    wherein the minimum flow state of the valve arrangement (20) allows an oxygen flow level that corresponds to a prescribed flow level for the patient when being at rest and the maximum flow state of the valve arrangement (20) allows an oxygen flow level corresponding to a prescribed flow level for a patient performing an activity,
    wherein said valve arrangement (20) comprises a restricting means (30) movable between a restricting position and an unrestricting position,
    wherein said restricting means (30) restricts the oxygen flow from said inlet (11) to said outlet (12) when said valve arrangement (20) is in the minimum flow state,
    wherein the restricting means (30) comprises tuning means for tuning the oxygen flow level through the valve arrangement (20) in said minimum flow state,
    wherein the portable control device is sized and adapted to be carried by the patient at all times, and
    wherein the portable control device is configured to always provide some flow of oxygen regardless of the setting of the actuator.

2. A portable control device (10) according to claim 1, wherein said valve arrangement (20) comprises a through hole (21) fluidly connecting said inlet (11) to said outlet (12), and said through hole (21) having a substantially round cross-section when seen in a plane being perpendicular to the through hole's general extension.

3. A portable control device (10) according to claim 1, wherein said restricting means (30) is slidable between said restricting position and said unrestricting position.

4. A portable control device (10) according to claim 1, wherein said tuning means comprises a threaded sleeve (31) and a tuning screw (32), wherein said tuning screw (32) when screwed in a first rotational direction increases the possible oxygen flow level through the valve arrangement (20) in said minimum flow state, and when screwed in a second rotational direction decreases the possible oxygen flow level through the valve arrangement (20) in said minimum flow state.

5. A portable control device (10) according to claim 4, wherein said valve arrangement (20) comprises a through hole (21) fluidly connecting said inlet (11) to said outlet (12), and said through hole (21) having a substantially round cross-section when seen in a plane being perpendicular to the through hole's general extension, and wherein said tuning screw (32) comprises a rounded screw tip (33) having a radius corresponding to the through hole (21) of said valve arrangement (20).

6. A portable control device (10) according to claim 5, wherein said valve arrangement (20) comprises a through hole (21) fluidly connecting said inlet (11) to said outlet (12), and said through hole (21) having a substantially round cross-section when seen in a plane being perpendicular to the through hole's general extension, and wherein an outer portion of said rounded screw tip (33) is removed so as to always allow some flow of gas through the through hole (21), even if the tuning screw is tightened all the way into the through hole (21).

7. A portable control device (10) according to claim 1, wherein said actuator (13) is restricted to two discrete possible positions, the first being the maximum position and the second being the minimum position.

8. A portable control device (10) according to claim 7, wherein the actuator position restriction is achieved by a spring loaded ball interacting with a groove having two seats and an intermediate ridge on said actuator.

9. An oxygen breathing system for providing a continuous gas flow to a patient, comprising;
    a portable control device according to claim 1,
    an oxygen source (50) fluidly connected to the inlet (11) of the portable control device (10) via a tube, and
    a breathing device (40) coupled to the outlet of the portable control device (10).

10. A portable control device according to claim 1, wherein the portable device has a weight of less than 100 gram.

11. A portable control device according to claim 1, wherein the portable device has a weight of less than 80 gram.

12. A portable control device according to claim 1, wherein the portable device has a weight of less than 60 gram.

13. A portable control device according to claim 1, wherein the portable device comprises a safety seal applied after tuning, so that the tuned minimum level may not be altered without breaking the safety seal.

14. A method for configuring a control device (10) for regulating a continuous oxygen flow to a patient from an oxygen source, wherein said method comprises the steps:
    determining (S1) a first desired oxygen flow ($F_{max}$) to a patient performing an activity,
    determining (S2) a second desired oxygen flow ($F_{min}$) to a patient resting,
    providing (S3) a portable control device (10) of claim 1 that, when in use, regulates a continuous gas flow to a patient from an oxygen source, said control device having a valve arrangement adjustable between a maximal flow and a tunable minimal flow, setting (S5) an oxygen flow level from the oxygen source so that it corresponds to the determined first desired oxygen flow ($F_{max}$), and tuning (S6) the minimum level of the portable control device (10) so that it corresponds to the determined second desired oxygen flow ($F_{min}$).

15. A method according to claim 14, after tuning the minimum level of the portable control device (10), safety sealing (S7) the portable control device (10) so that the tuned minimum level may not be altered without breaking the safety seal.

* * * * *